(12) United States Patent
Madsen

(10) Patent No.: US 7,833,475 B2
(45) Date of Patent: Nov. 16, 2010

(54) METHOD FOR STERILISING A MEDICAL DEVICE HAVING A HYDROPHILIC COATING

(75) Inventor: Niels Jorgen Madsen, Birkerod (DK)

(73) Assignee: Coloplast A/S, Humlebaek (DK)

( * ) Notice: Subject to any disclaimer, the term of this patent is extended or adjusted under 35 U.S.C. 154(b) by 293 days.

(21) Appl. No.: 11/919,792

(22) PCT Filed: May 2, 2006

(86) PCT No.: PCT/EP2006/061979

§ 371 (c)(1), (2), (4) Date: Nov. 2, 2007

(87) PCT Pub. No.: WO2006/117372

PCT Pub. Date: Nov. 9, 2006

(65) Prior Publication Data

US 2008/0292496 A1    Nov. 27, 2008

(30) Foreign Application Priority Data

May 2, 2005    (DK) .............................. 2005 00644

(51) Int. Cl.
A61L 2/00    (2006.01)
(52) U.S. Cl. .............................. 422/23; 422/22; 422/40
(58) Field of Classification Search .................. 422/22, 422/23, 40; 604/12, 265; 523/105
See application file for complete search history.

(56) References Cited

U.S. PATENT DOCUMENTS

| | | | |
|---|---|---|---|
| 3,648,704 A | 3/1972 | Jackson | |
| 3,967,728 A | 7/1976 | Gordon et al. | |
| 4,119,094 A | 10/1978 | Micklus et al. | |
| 4,373,009 A | 2/1983 | Winn | |
| 4,459,317 A | 7/1984 | Lambert | |
| 4,792,914 A | 12/1988 | Dartois et al. | |
| 5,001,009 A | 3/1991 | Whitbourne | |
| 5,041,100 A | 8/1991 | Bowland et al. | |
| 5,120,816 A | 6/1992 | Gould et al. | |
| 5,688,855 A * | 11/1997 | Stoy et al. .................. | 524/505 |
| 6,723,350 B2 * | 4/2004 | Burrell et al. ............... | 424/618 |
| 6,986,868 B2 * | 1/2006 | Madsen ....................... | 422/23 |
| 2002/0037943 A1 * | 3/2002 | Madsen ....................... | 522/86 |
| 2005/0214443 A1 | 9/2005 | Madsen | |

FOREIGN PATENT DOCUMENTS

| | | |
|---|---|---|
| DK | 159018 | 10/1983 |
| EP | 0 217 771 | 4/1987 |
| EP | 0 379 156 | 7/1990 |
| EP | 0 389 632 | 10/1990 |
| EP | 0 454 293 | 10/1991 |
| EP | 0 093 093 B2 | 11/1991 |
| EP | 1 131 112 | 9/2001 |
| GB | 1600963 | 10/1981 |
| GB | 2 284 764 | 6/1995 |
| JP | 4-285561 | 10/1992 |
| JP | 2002530158 | 9/2002 |
| WO | WO 86/06284 | 11/1986 |
| WO | WO 89/09246 | 10/1989 |
| WO | WO 90/05162 | 5/1990 |
| WO | WO 91/19756 | 12/1991 |
| WO | WO 94/16747 | 8/1994 |
| WO | WO 98/19729 | 5/1998 |
| WO | WO 98/58988 | 12/1998 |
| WO | WO 98/58990 | 12/1998 |
| WO | WO 00/30696 | 6/2000 |
| WO | WO 2004/075944 | 9/2004 |

* cited by examiner

*Primary Examiner*—Sean E Conley
(74) *Attorney, Agent, or Firm*—Jacobson Holman PLLC

(57) ABSTRACT

The present invention relates to sterilization of medical devices having hydrophilic coatings and more specific to sterilization of medical devices having a wetted hydrophilic coating using radiation. The medical devices sterilized according to the invention show, after sterilization using radiation, a prolonged water drain off time and reduced friction force.

24 Claims, No Drawings

METHOD FOR STERILISING A MEDICAL DEVICE HAVING A HYDROPHILIC COATING

FIELD OF THE INVENTION

The present invention relates to sterilisation of medical devices having hydrophilic coatings and more specific to sterilisation of medical devices having a wetted hydrophilic coating using radiation. The medical devices sterilised according to the invention show, after sterilisation using radiation, a prolonged water drain off time and reduced friction force.

DESCRIPTION OF THE RELATED ART

It is known to coat medical devices, e.g. catheters for introduction into human cavities such as blood vessels, digestive organs and the urinary system, with a hydrophilic coating, normally as a minimum applied on that part of the surface which is introduced or comes into contact with mucous membranes, etc., during introduction of the device. Whereas such coating is not particularly smooth when dry, it becomes extremely slippery when it is swelled with water, preferably immediately before introduction into the human body and thus ensures a substantially painless introduction with a minimum of damage on tissue.

U.S. Pat. No. 3,967,728 to Gordon discloses the use of a sterile lubricant for deposition on and lubricating an uncoated catheter before use.

WO 86/06284 (Astra Meditech Aktiebolag) discloses a wetting and storing device for a coated catheter in which the coating may be wetted using water or water comprising common salt and possibly bactericidal compounds or other additives.

GB patent application No. 2 284 764 (MMG (Europe Ltd)) discloses the application of a lubricious substance such as a water-based jelly to the tip of a non-coated catheter prior to insertion into the urethra.

U.S. Pat. No. 3,648,704 (Jackson) discloses a disposable catheter apparatus in which a lubricant may be applied to the tip of the catheter prior to catherisation.

A large number of methods are known for the production of hydrophilic surface coatings for improving the slipperiness of a catheter or other medical device. These methods are most often based on the fact that the substrate to be provided with a hydrophilic surface coating, in the course of one or more process stages with intermediary drying and curing, is coated with one or more (mostly two) layers, which are brought to react with one another in various ways, e.g. by polymerisation initiated by irradiation, by UV light, by graft polymerisation, by the formation of inter-polymeric network structures, or by direct chemical reaction. Known hydrophilic coatings and processes for the application thereof are e.g. disclosed in Danish Patent No. 159,018, published European Patent Application Nos. EP 0 389 632, EP 0 379 156, and EP 0 454 293, European Patent No. EP 0 093 093 B2, British Patent No. 1,600,963, U.S. Pat. Nos. 4,119,094, 4,373,009, 4,792,914, 5,041,100 and 5,120,816, and into PCT Publication Nos. WO 90/05162 and WO 91/19756.

According to a method disclosed in U.S. Pat. No. 5,001,009, a hydrophilic surface coating is prepared on a substrate by applying, in two stages or in one combined stage, on the substrate a primer reactive with or adhesive to the substrate and then the actual hydrophilic surface layer which, in this case, comprises polyvinylpyrrolidone as the active constituent. By this method, no chemical reaction takes place between the components of the two layers applied. When the product remains inside the body only for a short period, there may be a risk that water will be extracted from the hydrophilic surface coating and into the tissues of the surrounding mucous membranes etc., owing to a higher osmotic potential of said tissues. At the same time, there is a risk of abrasion of the coating during insertion. As a result of the extraction of water or loss of coating, the hydrophilic surface coating will have a tendency to become less slippery and to stick to surrounding tissues, and the removal of the medical device from the body may cause pain or damage the tissue. This is especially a problem when carrying out urodynamic examinations via a catheter.

European Patent No. EP 0 217 771 describes a method of forming a hydrophilic coating in order to retain the slipperiness in use for a longer period of time by applying a non-reactive hydrophilic polymer surface layer to a substrate, applying to the non-reactive hydrophilic surface polymer a solution comprising a solvent and above 2% (weight per volume) of an osmolality-increasing compound selected from the group consisting of mono and disaccharides, sugar alcohols, and non-toxic organic and inorganic salts, with the proviso that the osmolality-increasing compound is not a trihalogenide such as KI3 (KI/I2), and evaporating the solvent. EP 0 217 771 discloses that when wetting the catheters after drying, catheters having a coating comprising a non-toxic, osmolality increasing compound retaining their slipperiness for longer times than corresponding untreated surfaces i.e. coated catheters dry more slowly. However EP 0 217 771 is silent with respect to storing the coated catheters in a wetted form or sterilisation or problems in connection herewith.

WO 94/16747 discloses a hydrophilic coating with improved retention of water on a surface, especially a surface of a medical device such as a urethra catheter, prepared by applying to the surface in one or more process steps at least one solution of components that will combine to form the hydrophilic coating. During the final step, the surface is coated with an osmolality promoting agent which is dissolved or emulgated in the solution or in the last solution to be applied when forming the hydrophilic coating. WO 94/16747 does not disclose cross-linked coatings.

WO 89/09246 discloses solid shaped structures having a surface coated with cross-linked hydrophilic polymer, the coating being durable and exhibiting a low coefficient of friction when wet. It is stated that the degree of cross-linking is critical and is to be controlled by the operating conditions chosen as too much cross-linking reduces or completely eliminates the low friction surface property, and too little cross-linking negatively affects the durability of the coating. WO 89/09246 does not disclose the presence of a water soluble or osmolality-increasing compound in the coating.

All said coatings are developed for instant swelling immediately before use of the medical device on which the coatings are applied.

It has been found, however, that most hydrophilic coatings lose their water retention and that the coefficient of friction increases when the coatings are stored in water for an extended period of time and/or particularly after sterilisation using irradiation or autoclaving.

It is described in EP 1 131 112 that the water retention can be increased dramatically and the initial coefficient of friction can be kept low by carrying out sterilisation of a medical device having a hydrophilic coating while in contact with an aqueous solution comprising hydrophilic polymers for example polyvinylpyrrolidone or copolymers containing N-vinylpyrrolidone, poly(meth)acrylic acid or copolymers containing (meth)acrylic acid or (meth)acrylic acid esters, polyacrylamides, polyvinylalcohol and copolymers of partially saponified vinylacetate copolymers, polyethylenglycol, polyvinylmethylether, polyvinylmethylethermaleic anhydride and copolymers containing maleicanhydride or maleicacidesters or copolymers containing vinylmethylether, or copolymers thereof, or water soluble polysaccharides or derivatives thereof such as carboxymethylcellulose (CMC) or hydroxyethylcellulose or Xanthane or a derivative thereof. Thus, it seems that the hydrophilicpolymers protect the above mentioned properties during exposure to sterilisation using radiation when wetted with such a polymer solution.

However, there is still a need for methods for providing a sterilised medical device with a hydrophilic coating. Also there is a need for new ways of providing the hydrophilic polymer in a sufficient amount in the aqueous wetting liquid for the sterilisation to be carried out without detrimental effect to the water retention and the initial friction of the coating.

SUMMARY OF THE INVENTION

The present application discloses various ways for protecting a hydrophilic coating during sterilisation by radiation. The protection provided maintains a high water retention and a low friction when the medical device with a hydrophilic coating is stored in water. The protection is provided by adding hydrophilic polymer(s) to the storage medium (the aqueous liquid) prior to sterilization. Whether the hydrophilic polymer(s) are added with the medical device (as proposed by adding the polymer(s) in dissolvable form to the medical device) or as a power or table does not affect the protective effect.

DETAILED DESCRIPTION OF THE INVENTION

One aspect of the invention relates to a method for sterilising a medical device having a hydrophilic coating comprising the steps of:
A) providing a medical device having a hydrophilic coating;
B) immersing said medical device having a hydrophilic coating in an aqueous liquid;
C) dissolving hydrophilic polymer(s) in said aqueous liquid; and
D) sterilising the device by applying a sufficient amount of radiation.

Normally, a loss of water retention capability of coated catheters is observed, probably due to loss of non-crosslinked and non-bonded polymer chains from the coating during storage in water or by further crosslinking of the coating during irradiation in water.

In the first case a collapse of the coating, when the device is removed from the water reservoir, will give a low water retention and increase of the coefficient of friction during use. In the second case further cross-linking will decrease the water content in the coating and hence, the coating will show a low water retention and an increased friction coefficient.

Using the invention it has proven possible to obtain and retain very high water drain off time and low initial friction force. It has surprisingly been found that by using the sterilisation method of the invention, it is possible to provide a medical device, such as a catheter, which is permanently wetted and thus ready to use and which may be sterilised by irradiation or autoclaving and which will retain the water retention capability and thus low coefficient of friction when the coatings are stored in water for an extended period of time.

In one embodiment of the invention the sterilisation is carried out while the medical device, suitably a catheter is immersed in the aqueous liquid within the package to be provided to the customer. The present method eliminates the need for special preparation of a swelling medium with the hydrophilic polymer(s). This swelling medium preparation process typically requires special reactor mixing equipment. The stability of the swelling medium is rather limited and very voluminous.

The present method provides an alternative method for protecting a medical device having a hydrophilic coating during radiation of said medical device by dissolving hydrophilic polymer(s) in an aqueous liquid after the medical device has been immersed into the aqueous liquid.

One advantage of the present method is that it allows the aqueous medium and the hydrophilic polymer(s) to be stored separately and just mixed when needed. This prolongs the shelf-life of each of the products and simplifies the logistics in a production plant.

Another advantage of the present method is that the level of degradation of the polymer is kept at a minimum. Dissolving the hydrophilic polymer(s) in small amounts takes place during the normal handling of the bags during closing and transportation—even just sitting on the shelf. Thus, the degradation due to e.g. stirring, heat generation, and oxidation is avoided.

The medical device may be selected from the group consisting of catheters, endoscopes, laryngoscopes, tubes for feeding, tubes for drainage, guide wires, condoms, urisheaths, barrier coatings, stents and other implants, extra corporeal blood conduits, membranes, blood filters, devices for circulatory assistance, dressings for wound care, and ostomy bags. Currently most relevant medical devices or medical device elements are catheters and catheter elements.

In one aspect of the invention the sterilization by radiation is performed by γ- or β-radiation (beta- or gamma-radiation).

In one aspect of the invention the medical device in step A), has a layer comprising non-covalently bound hydrophilic polymer(s) such that upon immersing the medical device, the non-covalently bound hydrophilic polymer(s) are allowed to dissolve in the aqueous liquid. In one embodiment the solution of hydrophilic polymer is applied to the hydrophilic coating by immersing the medical device with the hydrophilic coating into the polymer solution followed by withdrawal at of the medical device with the hydrophilic coating with a speed leaving a sufficiently large amount of non-covalently bound hydrophilic polymer as a layer on the medical device with the hydrophilic coating. In terms of processing this 'extra dipping' is preferably performed while handling the medical device. Hereby a separate step of applying the hydrophilic polymer(s) to the aqueous solution is replaced with the extra dipping step. In processing terms, an individual handling step has been removed, saving processing time.

Such medical device having a layer comprising non-covalently bound hydrophilic polymer(s) can be obtained by:
IIIa) providing a medical device having a hydrophilic coating;
IIIb) providing a polymer solution comprising at least one hydrophilic polymer and at least one solvent;
IIIc) applying said polymer solution to said hydrophilic coating;
IIId) optionally evaporation at least part of the solvent(s) from said polymer solution present on said hydrophilic coating.

In order to add a sufficiently thick layer of non-covalently bound hydrophilic polymer to the hydrophilic coating in step IIIb) is necessary to have a sufficiently concentrated solution of the hydrophilic polymer.

The optimal amount will depend on the specific hydrophilic polymer(s) in question and a person skilled in the art will be able to determine the optimal amount of hydrophilic polymer(s) in the solution.

The solvent used for the polymer solution used in step IIIb) comprising one or more hydrophilic polymers may be selected from water, or, preferably, ethanol or other alcohols, or mixture thereof. However, any solvent can in principle be used. Other suitable solvents may be selected from methylethylketon, diethylether, dioxan, hexan, heptan, benzol, toluol, chloroform, dichlormethan, tetrahydrofuran and acetonitril, 1,3-dioxolane and other ethers, acetone and other ketones, di-methylsulfoxide and other sulfoxides, dimethyl formamide and other amides, N-methyl-2-pyrrolidone and other lactams, glycols, glycol ethers, glycol esters, other esters, amines, heterocyclic compounds, alkylated urea derivatives, liquid nitriles, nitroalkanes, haloalkanes, haloarenes, trialkyl phosphates, dialkyl alkanephosphonates, and other commonly known organic solvents, or mixtures thereof.

The polymer solution for step IIIb) may also contain other ingredients, for example compounds, which are useful for increasing the osmolality of the hydrophilic surface.

The polymer solution applied in step IIIc) may be applied by conventional techniques (dipping, spraying, incubation, rolling etc.) and may optionally subsequently be dried by evaporation of solvents.

Another feature, which is important for the amount of hydrophilic polymer which may be layered in step IIIc) is the speed at which the medical device with the hydrophilic coating is removed from the polymer solution. The optimal speed depends on the particular polymer solution and the amount of non-covalently bound polymer needed on the surface of the hydrophilic coating and may be determined by a person skilled in the art.

One aspect of the invention allows the step of dissolving the hydrophilic polyer(s) in the aqueous liquid to be a passive dissolving process, that is no active stirring in the aqueous liquid.

In one embodiment the hydrophilic polymer(s) to be dissolved are in power form.

In one embodiment, the hydrophilic polymer(s) could be added as a solid, such as in tablet form, e.g. in step IIc). The advantage of the use of tables is that the risk of the working environment being contaminated with dust is reduced when operating with tables.

One aspect of the invention relates to a method for sterilising a medical device having a hydrophilic coating comprising the steps of:

Ia) providing a medical device having a hydrophilic coating, said coating having a layer comprising non-covalently bound hydrophilic polymer(s);
Ib) applying an aqueous liquid to said hydrophilic coating;
Ic) allowing non-covalently bound hydrophilic polymer(s) to dissolve in the aqueous liquid; and
Id) sterilising the device by applying a sufficient amount of radiation, or IIa) providing a medical device having a hydrophilic coating;
IIb) immersing said hydrophilic coating in an aqueous liquid;
IIc) dissolving hydrophilic polymer(s) in said aqueous liquid; and
IId) sterilising the device by applying a sufficient amount of radiation.

As would appear from the above, this aspect of the invention relates to two related methods for sterilising a medical device having a hydrophilic coating, namely the method according to steps Ia)-Id) where the hydrophilic polymer(s) needed during the sterilisation process is carried as a layer on top of the hydrophilic coating and at least part of the hydrophilic polymer(s) is dissolved in the aqueous liquid before sterilisation. The other method according to process steps IIa)-IId), the hydrophilic polymer is added to the aqueous liquid after the medical device with the hydrophilic coating has been immersed into the aqueous liquid.

Suitably, the aqueous liquid in step Ib) is applied to the hydrophilic coating of the device in step Ia) by immersing the hydrophilic coating in the aqueous liquid.

The hydrophilic polymer is suitably a synthetic polymer. Such hydrophilic polymers may be selected from the group consisting of polyvinylpyrrolidone or copolymers containing N-vinylpyrrolidone, poly(meth)acrylic acid or copolymers containing (meth)acrylic acid or (meth)acrylic acid esters, polyacrylamides, polyvinylalcohol and copolymers of partially saponified vinylacetate copolymers, polyethylenglycol, polyvinylmethylether, polyvinylmethylethermaleic anhydride and copolymers containing maleicanhydride or maleicacidesters or copolymers containing vinylmethylether. In an especially preferred embodiment of the invention the hydrophilic polymer is a polyvinyl pyrrolidone (PVP), such as PVP K-25.

The amount of polyvinyl pyrrolidone to be used according to the invention may vary and depends i.a. on the molecular weight of the specific PVP. The higher the molecular weight, the higher is the tendency of gelling. Thus, the use of higher amounts of low molecular weight PVP gives an effect similar to the use of lower amounts of a higher molecular weight PVP. The amount of a PVP of a given molecular weight PVP to be used is easily determined by the skilled in the art by routine experiments testing the water retention.

When using a PVP having a relatively low molecular weight above 1000 and preferably above 5000, an amount of 6% by weight when initiating sterilisation has proven to be suitable giving a long retention time, a low friction and no problems with gelling.

It is also considered an aspect of the invention, when working with medical devices having physically bound or cross-linked hydrophilic coatings, to use a hydrophilic polymer not forming cross-links with the coating.

PEG 2000 is a thermoplastic and a uniquely tablet-forming polymer. PEG is a very inexpensive material compared to PVP. In a preferred embodiment, the hydrophilic polymer is polyethylenglycol (PEG) or a copolymer thereof.

Alternatively, the hydrophilic polymer is a polysaccharide. Suitably, the hydrophilic polymer is selected from the group consisting of water soluble polysaccharides, such as carboxymethylcellulose (CMC) or hydroxyethylcellulose and Xanthane or a derivative thereof.

In a preferred embodiment of the invention the hydrophilic polymer is CMC or a derivative thereof. The concentration of CMC in the aqueous solution when initiating sterilisation is suitably from 0.005 to 3.0%, depending on the molecular weight and degree of substitution of the polymer, preferably about 0.5% giving very good results. When using xanthan, the amount is normally in the range from 0.005 to 1%, preferably about 0.15%.

In one embodiment the hydrophilic polymers are mixtures of the preferred species stated above.

It is preferred that the hydrophilic polymer is a synthetic polymer and especially that the hydrophilic polymer is at least compatible with and preferably of the same type as the hydrophilic polymer of the coating.

Also preferred are polysaccharides selected from the group consisting of cellulose derivatives and xanthans. Although polysaccharides show a tendency of break down on sterilisation using radiation, these compounds have still proven effective in giving a long retention time, a low friction. Normally such compounds show a very pronounced thickening effect in water and are used in relatively low amounts.

A sufficient amount of hydrophilic polymer(s) should be allowed to dissolve in the aqueous liquid before sterilisation is carried out.

The amount of non-covalently bound hydrophilic polymer comprised in the hydrophilic coating in step Ia) and the amount of aqueous liquid used in step Ib) is selected so that after sterilisation, the initial friction and the water retention is above 3 minutes and the initial friction is below 0.05 N when measured using the standard test ASTM D 1894-93 as described herein.

Likewise, the amount of hydrophilic polymer added to the aqueous liquid in step IIc) compared to the amount of aqueous liquid is such that the initial friction and the water retention is above 3 minutes and the initial friction is below 0.05 N when measured using the standard test ASTM D 1894-93 as described herein.

The optimal amount will depend on the specific hydrophilic polymer(s) in question and a person skilled in the art will be able to determine the optimal amount of hydrophilic polymer(s) needed before sterilisation is initiated.

Suitably, the medical devices are immersed in the aqueous liquid within the package which is delivered to the customer, and the device is sterilised while packed in said package.

The invention thus provides a package comprising a sterilised medical device having a wetted hydrophilic coating. Thus, catheters which are sterilized and permanently wetted by the aqueous liquid and thus ready to use are provided. Such package may be of the kind disclosed in WO 98/19729.

The medical device to be sterilised according to the invention may have a physically cross-linked hydrophilic coating or a covalently cross-linked hydrophilic coating as described in the references described above.

A catheter having crosslinked two-layer hydrophilic coating may be prepared by a method comprising the steps of
a) preparing a solution of polyvinyl pyrrolidone dissolved in an ethanol/gamma butyrolactone solvent mixture,
b) dipping a raw catheter in the solution and letting it dry at ambient temperature,
c) dipping the resulting catheter in a PVP-solution containing urea and an ethanol/gamma butyrolactone (85/15) solvent mixture,
d) further drying at elevated temperature,
e) cross-linking the polyvinylpyrrolidone by exposing the coated catheter to UV-light having a wave length range between 200 and 300 nm. for from ½ to 15 minutes.

A catheter carrying a crosslinked hydrophilic coating with unsaturated Poly(methyl vinyl ether/maleic anhydride)/hydroxyethylmethacrylate (HEMA) pre-polymers may be prepared by a method comprising the steps of
a) preparing a solution of poly(methyl vinyl ether/maleic anhydride) in acetone in a reaction vessel equipped with at stirrer, keeping the reaction mixture at room temperature while adding 1-methylimidazole as a catalyst and hydroxyethyl-methacrylate dropwise to the stirred polymer solution during a period of 30 minutes,
b) stirring the mixture for from few minutes to 10 hours at room temperature,
c) preparing a primer mixture by dissolving a medical grade polyurethane and the poly(methyl vinyl ether/maleic anhydride)/HEMA unsaturated prepolymer in a mixture of THF and acetone,
d) coating a raw catheter with a primer by dipping in the resulting solution in a manner known per se,
e) dipping the resulting catheter in the solution of poly(methyl vinyl ether/maleic anhydride)/HEMA unsaturated prepolymer in acetone for applying a top coat,
f) drying the resulting catheter,
g) cross-linking the poly(methyl vinyl ether/maleic anhydride)/HEMA unsaturated prepolymerpolyvinylpyrrolidone by exposing the coated catheter to 5 M rads from a high energy electron beam source.

A catheter having a cross-linked single layer of hydrophilic coating may be prepared by a method comprising the steps of
a) preparing a solution of polyvinyl pyrrolidone dissolved in an ethanol/gamma butyrolactone solvent mixture,
b) dipping a raw catheter in the solution and letting it dry at elevated temperature,
c) cross-linking the polyvinylpyrrolidone by exposing the coated catheter to UV-light having a wave length range between 200 and 300 nm. for from ½ to 15 minutes.

According to the invention, the above mentioned catheters having hydrophilic coatings are subjected to the method steps IIIa)-IIId) and subsequently to method steps Ia)-Id) as described above, or to method steps IIa)-IId) as described above in order to achieve a sterilised medical device.

The solution comprising the hydrophilic polymer and/or the aqueous liquid used according to the invention may comprise an antibacterial agent such as a silver salt, e.g. silver sulphadiazine, an acceptable iodine source such as povidone iodine (also called polyvinylpyrrolidone iodine), chlorhexidine salts such as the gluconate, acetate, hydrochloride or the like salts or quaternary antibacterial agents such as benzalkonium chloride or other antiseptics or antibiotics. Antibacterial agents reduces the risk of infection, especially when performing urodynamic examinations.

The solution of hydrophilic polymer(s) and/or the aqueous liquid used according to the invention may also comprise an osmolality increasing agent such as urea, sodium chloride and/or any salt or organic low molecular weight compound being physiological acceptable and non-irritating for adjusting the ion strength of the coating approximately to the physiological range, the coating preferably being isotonic in use.

Compounds useful for increasing the osmolality of the hydrophilic surface may be selected from glucose, sorbitol, sodium chloride, sodium citrate, sodium benzoate, calcium chloride, potassium chloride, potassium iodide, potassium nitrate an urea.

Saline or another non-toxic osmolality increasing agent is preferably present in the amounts suggested in the references cited above. Thus, saline is preferably present in an amount of 0.9%.

When using urea, the added amount may vary within very broad limits.

The solution of hydrophilic polymer(s) and/or the aqueous liquid used according to the invention may also, if desired, comprise plasticizers for the hydrophilic coating such as diethylene glycol, glycerol, phthalates, sorbitol or the like.

Indicators or buffers for pH or antibodies, e.g. monoclonal antibodies for specific proteins, may also be comprised in the solution of hydrophilic polymer(s) and/or the aqueous liquid.

Pharmaceutically active compounds such as antioxidants or preservatives such as anti microbial agents or antithrombogenic agents may be added to the solution of hydrophilic polymers and/or aqueous liquid used according to the invention.

The additives or other ingredients mentioned above may be added to the solution of hydrophilic polymer and/or the aqueous liquid at any time during process covered by the present invention.

EXAMPLES

Materials and Methods

Polyvinylpyrrolidone: PVP K 90 available from ISP Inc. having a molecular weight 1,300,000 according to ISP.

Polyvinylpyrrolidone: Plasdone K-25 (Povidone, USP) available from ISP Inc. having a molecular weight 34,000 according to ISP.

Poly(methyl vinyl ether/maleic anhydride) is available as the Gantrez AN series of copolymers from ISP.

Ethanol: Absolute Alcohol.

Gamma butyrolactone: Gamma-butyrolactone from International Speciality Products.

UV catalyst: ESACURE KIP 150 from Lamberti SpA.

Darocure® 1173 from Ciba Geigy.

Plasdone K-25 from ISP.

Plasdone C-15 (Povidone, USP) from ISP.

Polyglycol 2000 from Clariant.

Test Equipment:

IR tablet press

Texture Analyzer TA:XT plus, Stable Micro Systems with a friction force test set up.

Method for Determination of the Friction.

The Standard Test Method for Static and Kinetic Coefficient of Friction of Plastic Film and Sheeting, ASTM D 1894-93 was modified for testing the friction coefficient and wear on plastic tubes and catheters.

Four swelled catheters were hung vertically by the connector, that is with the eyes towards the bottom. The fifth catheter was immediately attached to a steel syringe connected to the TA friction measurement device. The catheter was placed on a polished steel block, and another polished steel block weighing 266.3 g was placed on top of the catheter. The reported friction was the average friction force (N) measured for two runs of the steel blocks along the catheter in each direction; this took about 1 minute. At t=2, 4, 6 and 8 minutes the procedure was repeated with a new catheter that had been hanging vertically for the specified amount of time. 13 runs were made for each type of catheter.

Method for Determination of Water Retention

Water retention was determined by subjectively determining the time for the liquid to drain off after which the coating is dry using a stop watch.

Example 1

Preparation of a Catheter Having a Crosslinked Two-Layer Hydrophilic Coating 5 parts of PVP K 90 and 0.05 parts of ESACURE KIP 150 were dissolved in 94.95 parts of an ethanol/gamma butyrolactone solvent mixture. PVC-catheters were dipped in the solution and dried 1 minute at ambient temperature and then dipped in a PVP-solution containing 5 parts of PVP, 1 part of urea and 94 parts of an ethanol/gamma butyrolactone (85/15) solvent mixture. The catheters were further dried for 30 minutes at 700 C and exposed to UV-light having a wave length range between 200 and 300 nm. for 5 minutes.

Example 2

Preparation of a Catheter Having a Crosslinked Hydrophilic Coating with Unsaturated Poly(Methyl Vinyl Ether/Maleic Anhydride)/Hydroxyethylmethacrylate (HEMA) Prepolymers 20 parts of Gantrez® AN 119 was dissolved in 200 parts of acetone in a reaction vessel equipped with at stirrer. The reaction mixture was kept at room temperature. One drop of 1-methylimidazole was added to the solution as a catalyst. 5 mole % 2-hydroxyethylmethacrylate, based on contents of maleic anhydride were added dropwise to the stirred polymer solution during a period at 30 min. The mixture was stirred for further 2 hours at room temperature.

A 50:50 primer mixture with 5% solids was prepared by dissolving a medical grade polyurethane and the Poly(methyl vinyl ether/maleic anhydride)/HEMA unsaturated prepolymer in a 50:50 mixture of THF and acetone and was coated on PVC catheters as a primer by dipping in a manner known per se.

The catheters were dipped in the solution of poly(methyl vinyl ether/maleic anhydride)/HEMA unsaturated prepolymer in acetone for applying a top coat, dried and exposed to 5 M rads from a high energy electron beam source.

Afterwards, the cross-linked coatings were hydrolysed and neutralised in a sodium hydrogen carbonate buffer solution for one hour before drying.

Example 3

A top coat and a primer solution were prepared as in Example b. To the solutions was added 1% by weight of the solid Darocure® 1173, a UV photo-initiator obtainable from Ciba Geigy.

PVC catheters were dipped in the primer solution, dried for 30 minutes and dipped in the top coat solution also containing 1% by weight of the solid of Darocure® 1173 and dried for further 30 minutes. Then, the coating was cross-linked by exposure to UV light.

The cross-linked coatings were then hydrolysed and neutralised in a sodium hydrogen carbonate buffer solution for one hour before drying.

Example 4

Preparation of a Catheter Having a Cross-Linked Single Layer Hydrophilic Coating According to the Invention 5 parts of PVP K 90 was dissolved in 95 parts of a ethanol/gamma butyrolactone (85/15) solvent mixture. PVC catheters were dipped in the solution, dried for 30 minutes at 700 C and exposed to a UV light having a wave length between 200 and 300 nm for 6 minutes.

Example 5

A layer comprising a hydrophilic polymer may be applied to the hydrophilic coating of the catheters prepared according to examples 1-4 by dipping the catheters in a solution comprising a hydrophilic polymer as described above.

The catheters are removed from the solution of hydrophilic polymer(s) and the solvent of the solution is optionally evaporate off (at least to a certain extend).

The dry catheters having a layer of hydrophilic polymer is then immersed in an aqueous liquid and sterilised by radiation.

Suitably, the catheters are immersed in the aqueous liquid within the package, which is delivered to the customer, and the device is sterilised while packed in said package.

Example 6

Pre-Coated Catheters are Coated with an Extra Layer

The purpose of the investigation described in the next series of examples is to compare four different methods for the preparation of the swelling medium to protect the coating of a catheter during sterilization by g- or b-radiation. As an example is used the SpeediCath coating (Coloplast A/S, Denmark).

The four methods are:
A. Applying by dipping an extra layer of low molecular weight and non-covalently bonded PVP on precoated catheters
B. Packing coated catheters together with PVP powder and saline solution
C. Packing coated catheters together with PVP as tablets and saline solution
D. Packing coated catheters together with PVP dissolved in a saline solution

TABLE 1

Pre-coated catheters are coated with an extra layer of low molecular weight and non-covalently bonded PVP in the following solutions.

| Recipe no. Materials | Swell 1 (%) | Swell 2 (%) | Swell 3 (%) | Swell 4 (%) | Swell 5 (%) | Swell 6 (%) |
|---|---|---|---|---|---|---|
| PVP C15 | 20 | 30 | 40 | — | — | — |
| PVP K25 | — | — | — | 20 | 30 | 40 |
| DI-water | 90 | 80 | 70 | 90 | 80 | 70 |
| Total | 100 | 100 | 100 | 100 | 100 | 100 |

1. 6 PVP K25 and C-15 mixtures are prepared as shown in table 1.
2. 8 pre-coated and non-sterile catheters are coated in each swelling medium/PVP-solution. Constant speed: 25 mm/s.
3. The catheters are dried at 90° C. for 1 hour or until a constant weight is achieved.
4. The coated catheters are stored individually in aluminum foil packaging with 10 ml isotonic water (saline solution).
5. All the products are β-sterilized with 50 kGy (2×25 kGy).
6. The friction force and the water retention are measured.

Example 7

Pre-Coated Catheters Stored with Saline Solution, and PVP Powder is Added 1. 8 pre-coated and non-sterile catheters are stored separately in 10 ml of isotonic water (saline solution) and 600 mg of PVP C-15 is added to each catheter.
2. 8 pre-coated and non-sterile catheters are stored separately in 10 ml of isotonic water (saline solution) and 600 mg of PVP K-25 is added to each catheter.
3. The PVP powder forms a clear solution typically within 24 hours or within 5-10 minutes by shaking the packaging.
4. The products are β-sterilized with 50 kGy (2×25 kGy).
5. The friction force and the water retention are measured.

Example 8

Pre-Coated Catheters Stored with Saline Solution, and Added PVP or PEG Tablets are Added 1. Tablets containing 600 mg of either PVP C15, PVP K25 or PEG 2000 are prepared by the IR press.
2. 8 pre-coated and non-sterile catheters are stored separately in 10 ml of isotonic water (saline solution), and a tablet containing 600 mg of PVP C-15 is added to each catheter.
3. 8 pre-coated and non-sterile catheters are stored separately in 10 ml of isotonic water (saline solution), and a tablet containing 600 mg of PVP K-25 is added to each catheter.
4. 8 pre-coated and non-sterile catheters are stored separately in 10 ml of isotonic water (saline solution), and a tablet containing 600 mg of PEG 2000 is added to each catheter.
5. The PVP or the PEG 2000 tablets form a clear solution typically within 24 hours or within 5-10 minutes by shaking the packaging.
6. The products are β-sterilized with 50 kGy (2×25 kGy).
7. The friction force and the water retention are measured.

Example 9

Pre-Coated Catheters Stored in a Mixture of PVP Dissolved in a Saline Solution

TABLE 2

Recipe for different the swelling medium

| Materials | PVP dissolved in a saline solution % | Saline solution % |
|---|---|---|
| Plasdone PVP C-15 | 6.0 | 0 |
| NaCl, sodium chloride | 0.9 | 0.9 |
| DI-water | 93.1 | 99. |
| Total | 100.0 | 100.0 |

TABLE 3

Friction force measured after drying for 0, 2, 4, 6 and 8 minutes.

| | Friction force (mN) | | | | |
|---|---|---|---|---|---|
| Air drying time in minutes | 0 | 2 | 4 | 6 | 8 |
| Example 6. A: Precoated catheters coated with an extra layer of low molecular weight and non-covalently bonded PVP. | | | | | |
| 20% PVP K-25 in water | 103 | 97 | 101 | 97 | 110 |
| 30% PVP K-25 in water | 89 | 94 | 85 | 107 | 115 |
| 40% PVP K-25 in water | 65 | 98 | 102 | 94 | 104 |
| 30% PVP C-15 in water | 59 | 55 | 82 | 63 | 70 |
| 40% PVP C-15 in water | 47 | 58 | 57 | 67 | 134 |
| Example 7. B: Precoated catheters stored with saline solution and added PVP powder | | | | | |
| PVP K-25 powder | 51 | 68 | 77 | 101 | 134 |
| PVP C-15 powder | 38 | 64 | 53 | 43 | 91 |
| Example 8. | | | | | |

TABLE 3-continued

Friction force measured after drying for 0, 2, 4, 6 and 8 minutes.

| Air drying time in minutes | Friction force (mN) | | | | |
|---|---|---|---|---|---|
| | 0 | 2 | 4 | 6 | 8 |
| C: Precoated catheters stored with saline solution and added PVP or PEG tablets | | | | | |
| PVP K-25 tablet | 66 | 59 | 80 | 71 | 92 |
| PVP C-15 tablet | 57 | 54 | 49 | 60 | 57 |
| PEG 2000 tablet | 61 | 81 | 74 | 94 | 79 |
| Example 9. D: Precoated catheters stored in a mixture of PVP dissolved in a saline solution | | | | | |
| PVP C-15 dissolved in a saline solution | 47 | 54 | 61 | 65 | 63 |
| Saline solution without PVP | 181 | 166 | 229 | 205 | 255 |

CONCLUSIONS

For all of the above experiments, it took about 24 h to get the hydrophilic polymer dissolved, when just sitting on the shelf. The handling of the bags prior to sterilization was sufficient to dissolve the PVP/PEG in the water.

The friction force and water retention after β-irradiation of reference catheters submerged in a swelling medium without low molecular weight hydrophilic polymers show much higher values compared to catheters prepared and stored according to the methods described in items A, B, C and D. In general, a friction of less than 150-200 mN is needed to insert the catheter.

Moreover, only minor differences in friction force and water retention were found after β-irradiation between the catheters prepared and stored according to the methods described in items A, B, C and D.

The invention claimed is:

1. A method for sterilizing a medical device having a hydrophilic coating comprising the steps of:
   A) providing a medical device having a hydrophilic coating;
   B) immersing said medical device in an aqueous liquid;
   C) dissolving at least one hydrophilic polymer in said aqueous liquid while said medical device is immersed in said aqueous liquid; and then
   D) sterilizing the device by applying a sufficient amount of radiation.

2. A method according to claim 1, wherein the medical device in step A) has a layer comprising at least one non-covalently bound hydrophilic polymer, such that upon immersing the medical device, the non-covalently bound hydrophilic polymer is allowed to dissolve in the aqueous liquid.

3. A method according to claim 1, wherein the hydrophilic polymer to be dissolved is in powder form.

4. A method according to claim 1, wherein the hydrophilic polymer to be dissolved is a tablet.

5. A method according to claim 1, wherein the aqueous liquid in step B is within a package which is delivered to a customer, and the device is sterilized while packed in said package.

6. A method according to claim 2, wherein the aqueous liquid in step B is within a package which is delivered to a customer, and the device is sterilized while packed in said package.

7. A method according to claim 3, wherein the aqueous liquid in step B is within a package which is delivered to a customer, and the device is sterilized while packed in said package.

8. A method according to claim 4, wherein the aqueous liquid in step B is within a package which is delivered to a customer, and the device is sterilized while packed in said package.

9. A method according to claim 1, wherein the hydrophilic polymer is a synthetic polymer.

10. A method according to claim 2, wherein the hydrophilic polymer is a synthetic polymer.

11. A method according to claim 3, wherein the hydrophilic polymer is a synthetic polymer.

12. A method according to claim 4, wherein the hydrophilic polymer is a synthetic polymer.

13. The method according to claim 9, wherein the hydrophilic polymer is selected from the group consisting of polyvinylpyrrolidone or copolymers containing N-vinylpyrrolidone, polyacrylic acid or copolymers containing acrylic acid or acrylic acid esters, polymethacrylic acid or copolymers containing methacrylic acid or methacrylic acid esters, polyacrylamides, polyvinylalcohol and copolymers of partially saponified vinylacetate copolymers, polyethyleneglycol, polyvinylmethylether, polyvinylmethylethermaleic anhydride and copolymers containing maleicanhydride or maleic acid esters or copolymers containing vinylmethyl ether.

14. The method according to claim 13, wherein the hydrophilic polymer is polyvinylpyrrolidone or a copolymer thereof.

15. The method according to claim 14, wherein the hydrophilic polymer is polyethylene glycol (PEG) or a copolymer thereof.

16. The method according to claim 10, wherein the hydrophilic polymer is selected from the group consisting of polyvinylpyrrolidone or copolymers containing N-vinylpyrrolidone, polyacrylic acid or copolymers containing acrylic acid or acrylic acid esters, polymethacrylic acid or copolymers containing methacrylic acid or methacrylic acid esters, polyacrylamides, polyvinylalcohol and copolymers of partially saponified vinylacetate copolymers, polyethyleneglycol, polyvinylmethylether, polyvinylmethylethermaleic anhydride and copolymers containing maleicanhydride or maleic acid esters or copolymers containing vinylmethyl ether.

17. The method according to claim 16, wherein the hydrophilic polymer is polyvinylpyrrolidone or a copolymer thereof.

18. The method according to claim 17, wherein the hydrophilic polymer is polyethylene glycol (PEG) or a copolymer thereof.

19. The method according to claim 11, wherein the hydrophilic polymer is selected from the group consisting of polyvinylpyrrolidone or copolymers containing N-vinylpyrrolidone, polyacrylic acid or copolymers containing acrylic acid or acrylic acid esters, polymethacrylic acid or copolymers containing methacrylic acid or methacrylic acid esters, polyacrylamides, polyvinylalcohol and copolymers of partially saponified vinylacetate copolymers, polyethyleneglycol, polyvinylmethylether, polyvinylmethylethermaleic anhydride and copolymers containing maleicanhydride or maleic acid esters or copolymers containing vinylmethyl ether.

20. The method according to claim 12, wherein the hydrophilic polymer is selected from the group consisting of polyvinylpyrrolidone or copolymers containing N-vinylpyrrolidone, polyacrylic acid or copolymers containing acrylic acid or acrylic acid esters, polymethacrylic acid or copolymers containing methacrylic acid or methacrylic acid esters, polyacrylamides, polyvinylalcohol and copolymers of partially saponified vinylacetate copolymers, polyethyleneglycol, polyvinylmethylether, polyvinylmethylethermaleic anhydride and copolymers containing maleicanhydride or maleic acid esters or copolymers containing vinylmethyl ether.

21. The method according to claim 1, wherein the hydrophilic polymer is a polysaccharide.

22. The method according to claim 21, wherein the hydrophilic polymer is selected from the group consisting of water soluble polysaccharides.

23. The method according to claim 22, wherein the hydrophilic polymer is selected from the group consisting of carboxymethylcellulose, hydroxyethylcellulose, Xanthane, or a derivative thereof.

24. The method according to claim 23, wherein the hydrophilic polymer is carboxymethylcellulose or a derivative thereof.

* * * * *